US011355225B2

(12) United States Patent
Schmidlin et al.

(10) Patent No.: US 11,355,225 B2
(45) Date of Patent: Jun. 7, 2022

(54) SYSTEM FOR USE OF A PHARMACEUTICAL PRODUCT (71) Applicant: Novartis AG, Basel (CH)

(72) Inventors: Main Schmidlin, Basel (CH); Mario Iobbi, Basel (CH); Erich Studer, Basel (CH); Andrew Bryant, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/493,733

(22) PCT Filed: Feb. 5, 2018

(86) PCT No.: PCT/EP2018/052787
§ 371 (c)(1),
(2) Date: Sep. 12, 2019

(87) PCT Pub. No.: WO2018/166710
PCT Pub. Date: Sep. 20, 2018

(65) Prior Publication Data
US 2020/0075149 A1 Mar. 5, 2020

Related U.S. Application Data (60) Provisional application No. 62/471,392, filed on Mar. 15, 2017.

(30) Foreign Application Priority Data

Mar. 31, 2017 (EP) ..................................... 17164171

(51) Int. Cl.
G16H 20/13 (2018.01)
G16H 20/17 (2018.01)
(Continued)

(52) U.S. Cl.
CPC ............. *G16H 20/13* (2018.01); *G16H 20/17* (2018.01); *G16H 40/63* (2018.01); *H04B 5/0031* (2013.01); *H04W 76/14* (2018.02)

(58) Field of Classification Search
CPC ........ G16H 20/13; G16H 20/17; G16H 40/63; H04W 76/14; H04B 5/0031; A61M 5/142;
(Continued)

(56) References Cited

U.S. PATENT DOCUMENTS 3,583,399 A 6/1971 Ritsky
5,957,889 A 9/1999 Poulsen et al.
(Continued)

FOREIGN PATENT DOCUMENTS

EP 2249274 A1 11/2010
EP 2987517 A1 2/2016
(Continued)

OTHER PUBLICATIONS

"Using RFID to Track Critical Medical Device Information: Vizinex." Vizinex RFID, Jul. 7, 2015, (6 pages), https://web.archive.org/web/20150711212300/https://www.vizinexrfid.com/using-rfid-track-critical-medical-device-information/.
(Continued)

Primary Examiner — Pablo N Tran
(74) Attorney, Agent, or Firm — Moore & Van Allen, PLLC; Henry B. Ward, III (57) ABSTRACT The present disclosure relates to a system (100) for use of a pharmaceutical product. The system comprises a container (102) accommodating a pharmaceutical product, the container (102) comprising a wireless communication unit (112) and a memory (116) which stores pairing-specific information for one or more medical devices (104), and a medical device (104) enabled for wireless communication with the
(Continued)

wireless communication unit (112) of the container (102) and configured to read the pairing-specific information from the memory (116) of the container (102) to verify whether the container (102) is permitted to be used by the medical device (104).

17 Claims, 4 Drawing Sheets

(51) Int. Cl.
   *G16H 40/63* (2018.01)
   *H04W 76/14* (2018.01)
   *H04B 5/00* (2006.01)

(58) Field of Classification Search
   CPC ......... A61M 39/10; A61M 5/14; G06F 19/00; G06K 19/077
   See application file for complete search history.

(56) References Cited

U.S. PATENT DOCUMENTS

| | | | |
|---|---|---|---|
| 8,035,517 B2 | 10/2011 | Gibson | |
| 8,123,724 B2 | 2/2012 | Gillespie, III | |
| 8,308,457 B2 * | 11/2012 | Rotem | A61M 5/14228 417/479 |
| 8,446,280 B2 | 5/2013 | Ortenzi et al. | |
| 9,452,267 B2 | 9/2016 | Reynolds et al. | |
| 9,750,896 B2 * | 9/2017 | Kamen | A61M 5/14244 |
| 9,789,245 B2 | 10/2017 | Tieck et al. | |
| 9,949,642 B2 * | 4/2018 | Love | A61B 5/002 |
| 10,137,246 B2 * | 11/2018 | Estes | G06F 19/00 |
| 10,357,603 B2 * | 7/2019 | Michaud | A61M 5/14248 |
| 10,380,321 B2 * | 8/2019 | Kamen | G16H 20/17 |
| 10,384,001 B2 * | 8/2019 | Nackaerts | G01F 13/006 |
| 2004/0051368 A1 | 3/2004 | Caputo et al. | |
| 2007/0073235 A1 | 3/2007 | Estes et al. | |
| 2010/0010443 A1 | 1/2010 | Morgan et al. | |
| 2010/0160857 A1 | 6/2010 | Pongpairochana et al. | |
| 2011/0166512 A1 | 7/2011 | Both et al. | |
| 2011/0264033 A1 | 10/2011 | Jensen et al. | |
| 2011/0306929 A1 | 12/2011 | Levesque et al. | |
| 2013/0211330 A1 | 8/2013 | Pedersen et al. | |
| 2013/0225945 A1 | 8/2013 | Prince et al. | |
| 2014/0142507 A1 | 5/2014 | Armes | |
| 2015/0001285 A1 | 1/2015 | Halbert et al. | |
| 2015/0126926 A1 | 5/2015 | Giambattista et al. | |
| 2015/0246176 A1 | 9/2015 | Navarro et al. | |
| 2015/0310185 A1 | 10/2015 | Shah | |
| 2016/0015885 A1 * | 1/2016 | Pananen | A61M 5/1456 604/111 |
| 2016/0051750 A1 | 2/2016 | Tsoukalis | |
| 2016/0082182 A1 | 3/2016 | Gregory et al. | |
| 2016/0175515 A1 | 6/2016 | McCullough | |
| 2017/0143902 A1 | 5/2017 | Hansen et al. | |
| 2017/0258986 A1 * | 9/2017 | Tsoukalis | A61M 5/14244 |
| 2019/0175841 A1 * | 6/2019 | Sjolund | A61B 5/7435 |

FOREIGN PATENT DOCUMENTS

| | | | | |
|---|---|---|---|---|
| EP | 3106190 A1 | 12/2016 | | |
| EP | 3217304 A1 * | 9/2017 | | G16H 10/60 |
| EP | 3388095 A1 * | 10/2018 | | A61M 5/1411 |
| EP | 3421064 A1 * | 1/2019 | | A61M 5/142 |
| FR | 2217026 A1 | 9/1974 | | |
| GB | 143084 A | 5/1920 | | |
| GB | 2145795 A | 4/1985 | | |
| JP | 2002366652 A | 12/2002 | | |
| JP | 2004503338 A | 2/2004 | | |
| JP | 2006034845 A | 2/2006 | | |
| JP | 2012005756 A | 1/2012 | | |
| JP | 2013097761 A | 5/2013 | | |
| JP | 2013533008 A | 8/2013 | | |
| JP | 2015213548 A | 12/2015 | | |
| JP | 2016535554 A | 11/2016 | | |
| WO | WO-2005072795 A2 | 8/2005 | | |
| WO | 2008004669 A1 | 1/2008 | | |
| WO | 2016014365 A1 | 1/2016 | | |
| WO | WO-2016033496 A1 | 3/2016 | | |

OTHER PUBLICATIONS

Center for Devices and Radiological Health. "Radio Frequency Wireless Technology in Medical Devices—Guidance." U.S. Food and Drug Administration, FDA, Aug. 14, 2013, (24 pages), https://www.fda.gov/regulatory-information/search-fda-guidance-documents/radio-frequency-wireless-technology-medical-devices-guidance-industry-and-fda-staff.

Fujitsu, "Application: Fujitsu RFID and Sensor Solution for Medical Device Traceability," https://www.fujitsu.com/us/Images/FUJITSU%20RFID%20for%20Medical%20Device%20Traceability.pdf, Aug. 2015, 2 pages.

International Search Report issued by the European Patent Office for International Patent Application No. PCT/EP2018/052787 dated Apr. 27, 2018.

Written opinion issued by the European Patent Office for International Patent Application No. PCT/EP2018/52787 dated Apr. 27, 2018.

International Preliminary Report on Patentability issued by the European Patent Office for International Patent Application No. PCT/EP2018/52787 dated Sep. 17, 2019.

Office Action issued by the Russian Patent Office for Russian Patent Application No. 2019127659/14(054287), dated Jun. 1, 2021.

Search Report issued by the Russian Patent Office for Russian Patent Application No. 2019127659/14(054287), dated May 31, 2021.

Office Action issued by the Japanese Patent Office for Japanese Patent Application No. 2019-550826, dated Feb. 28, 2022.

\* cited by examiner

SYSTEM FOR USE OF A PHARMACEUTICAL PRODUCT

CROSS REFERENCE TO RELATED APPLICATIONS

This application is a national stage entry, filed under 35 U.S.C. 371, of International Application No. PCT/EP2018/052787, filed on Mar. 15, 2018, which claims the benefit of and priority to U.S. Provisional Application No. 62/471,392, filed Mar. 15, 2017, and claims the benefit of and priority to European Patent Application No. 17164171.5, filed Mar. 31, 2017, the entire contents of which are hereby incorporated herein by reference in their entireties and for all purposes.

The present disclosure generally relates to the medical field. More particularly, the present disclosure relates to a system for use of a pharmaceutical product, a container accommodating a pharmaceutical product for use in the system as well as a medical device for use of the pharmaceutical product accommodated in the container.

In the medical field, the use of replaceable pharmaceutical product containers with standardized medical devices is generally known. In an example, a replaceable container that accommodates a pharmaceutical product to be administered to a patient may be inserted into an administration device so that the pharmaceutical product may be administered from the container to the body of the patient. The administration device may be an injection device, such as a syringe, for example, and the container may be a replaceable injection cartridge that contains a drug to be injected to the patient. In another example, a corresponding pharmaceutical product container may be used in connection with a reconstitution device for the purpose of preparing a liquid or lyophilized solution specifically adapted to the medication requirements of the patient and, hence, for subsequent administration.

Although pharmaceutical product containers are typically labeled in a clear manner to indicate to the user (e.g., a clinician or the patient) information regarding the pharmaceutical product and its proper use, it may still happen that the user confuses the container and applies it with a wrong medical device or, even worse, to the wrong patient, hence, potentially leading to non-adherence of use instructions given. Thus, in situations in which a pharmaceutical product is specifically prepared for a dedicated patient or, otherwise, in situations in which the pharmaceutical product is to be used in combination with a dedicated medical device, it is generally desired to prevent the user from unintended use of the container.

Patent application EP 2 987 517 A1 discloses a medication infusion safety device for assuring an application of a correct medication to a patient which comprises a memory means adapted to be provided at a medication reservoir containing a medication and to store data identifying said medication, a memory reading means adapted to be provided at an infusion pump unit and to read data from said memory means, and control means adapted to control an infusion in accordance with an evaluation of data read by said memory reading means so that only in case the evaluation leads to the result that the medication is correct it causes the infusion from said medication reservoir to be started, wherein said memory reading means is adapted to read data from said memory means through direct wireless connection.

Patent application EP 2 249 274 A1 relates to management of information relating to medical fluids, containers therefor, and medical fluid administration devices for administering such medical fluids to patients. Data tags (e.g., RFID tags) are associated with the containers and may be electromagnetically read from and/or written to using an electromagnetic device, for example, that may be associated with a medical fluid administration device.

It is an object of the present disclosure to provide techniques that assist in ensuring that a pharmaceutical product and its container are correctly applied.

According to aspects of the present disclosure, a system for use of a pharmaceutical product, a container accommodating a pharmaceutical product, and a medical device for use of a pharmaceutical product accommodated in a container are provided according to the independent claims. Preferred embodiments are recited in the dependent claims.

According to a first example of the present disclosure, a system for use of a pharmaceutical product is provided. The system comprises a container accommodating a pharmaceutical product. The container comprises a wireless communication unit and a memory which stores pairing-specific information for one or more medical devices. The system further comprises a medical device enabled for wireless communication with the wireless communication unit of the container and configured to read the pairing-specific information from the memory of the container to verify whether the container is permitted to be used by the medical device.

The pairing-specific information may be any kind of information which enables the medical device to confirm whether the container is allowed to be used in combination with the medical device or, in other words, to confirm whether the container may be paired with the medical device. In this way, it may be checked whether the container is paired with the right medical device before effectively using the pharmaceutical product contained in the container in a medical procedure and, hence, wrong use of the pharmaceutical product may be prevented. Further, since the memory of the container may store pairing-specific information for more than one medical device, the container may be prepared to interface with not only one, but with a plurality of medical devices. A system is thus achieved in which a universal container may be used in combination with a suite of dedicated devices. Performing the verification ensures that the medical device is one of the one or more medical devices for which pairing-specific information is stored on the memory of the container.

The medical device may be configured to block use of the pharmaceutical product until the verification is complete. If it is confirmed that the container may be paired with the medical device (hereinafter denoted as a "positive confirmation"), the medical device may release the block so that the medical device may proceed with the intended medical procedure. On the other hand, in case it is determined that the container may not be paired with the medical device (hereinafter denoted as a "negative confirmation"), the medical device may maintain the block and thus prevent use of the pharmaceutical product in the container in a medical procedure with the medical device. In either case, an indication of the result of the verification may be provided by the medical device, e.g., via text form on a display, through an audible output, or through dedicated visual indicators, such as LEDs, provided at the medical device.

The medical device may store pairing-specific information in a memory of the medical device itself in order to be able to perform the verification. Performing the verification may include comparing the pairing-specific information stored in the memory of the container with the pairing-specific information stored by the medical device. The medical device may decide on a positive confirmation if the pairing-specific information stored in the memory of the container and the pairing-specific information stored by the medical device match. It will be understood, however, that other ways of performing the verification, rather than such a simple match, are generally conceivable.

In certain variants, the pairing-specific information stored in the memory of the container may comprise, for each of the one or more medical devices, at least one of an identification of the respective medical device, an identification of a user to which the respective medical device is assigned, and at least one control parameter for controlling a function specific to the respective medical device. It will be understood that these examples are non-limiting and that any other type of information which enables the medical device to perform the verification may be used as the pairing-specific information.

In case the pairing-specific information stored in the memory of the container comprises an identification of the medical device (e.g., a device ID), the medical device may compare the identification to a corresponding identification (e.g., a device ID) stored on the medical device and decide on a positive confirmation, if both identifications match. In this case, the verification may be used to ensure that the container is used with the right medical device. Similarly, in case the pairing-specific information stored in the memory of the container comprises an identification of a user to which the medical device is assigned (e.g., a patient ID), the medical device may compare the identification to a corresponding identification (e.g., a patient ID) stored on the medical device and decide on a positive confirmation, if both identifications match. In this case, the verification may be used to ensure that the pharmaceutical product is used for the right patient. Further, in case the pairing-specific information stored in the memory of the container comprises at least one control parameter for controlling a function specific to the medical device, the at least one control parameter may be necessary for the medical device to configure its own operation. Detection of the non-presence of the at least one control parameter in the memory of the container may thus result in a negative confirmation. If the medical device is an automated injection device, the at least one control parameter may be used by the injection device to configure the injection speed of the pharmaceutical product from the container, for example.

In one variant, the identification of the medical device and/or the at least one control parameter may be specific to the medical device, i.e., specific to a particular instance of a medical device type. In this case, the container may be used in combination with a dedicated device only. The medical device types may include, e.g., a syringe, an automated injection device, a patch pump device, a reconstitution device, or the like. In another variant, the identification of the medical device and/or the at least one control parameter may be specific to a device type of the medical device, i.e., specific to all instances of a medical device type. In this case, the container may be used in combination with any device of a dedicated medical device type.

The wireless communication unit of the container may be a passive wireless communication unit. In one variant, the wireless communication unit may be a Near Field Communication (NFC) unit and may comprise an RFID tag, for example. If the container comprises a label, the wireless communication unit and/or the memory may be included in the label. The medical device may be an NFC enabled device which is configured to read the pairing-specific information from the memory of the container via NFC. It will be understood that other types of wireless communication technologies are conceivable for the same purpose. It is even conceivable that the wireless communication unit may be an active unit, given that corresponding power supply is provided. It will also be understood that the medical device may not only read from the memory of the container, but may also write to the memory of the container, e.g., to set or update certain information stored in the memory of the container (examples for this will be given further below).

The pairing-specific information stored in the memory of the container may be defined by the manufacturer of the pharmaceutical product and may be written to the memory of the container at an initial stage of the lifecycle of the pharmaceutical product and the container. The pairing-specific information stored in the memory of the container may also be written to the memory of the container at a later stage in the lifecycle of the pharmaceutical product, such as when the container is handed over to a patient in a pharmacy, for example. The same applies to the pairing-specific information stored on the medical device. The pairing-specific information stored on the medical device may be defined by the manufacturer of medical device and may be written to the memory of the medical device at the time of manufacturing. The pairing-specific information stored on the medical device may also be written to the memory of the medical device at a later stage, such as when the medical device is handed over to a patient in a pharmacy, for example. This may particularly be the case, when the medical device is a device for one-time use, such as a one-time use syringe or other injection device which is to be disposed after a single use, for example.

For the purpose of writing into the memory of the medical device, the medical device may comprise a communication unit. The pairing-specific information may in this case be written from an external configuration device to the medical device via the communication unit. The communication unit may be a passive wireless communication unit, e.g., an NFC unit included in the medical device. The external configuration device may be an NFC enabled device which is configured to write the pairing-specific information to the memory of the medical device via NFC. It will be understood that other types of communication technologies (both wired and wireless) are conceivable for the same purpose.

Further than storing pairing-specific information, the memory of the container may also be employed to store additional information which may be relevant to the pharmaceutical product accommodated in the container. In one such variant, the memory of the container may store a usage scheme specifically adapted to the pharmaceutical product accommodated in the container, wherein the usage scheme specifies at least one usage-related parameter to be adhered to in using the pharmaceutical product. The medical device may be configured to read the usage scheme from the memory of the container and to perform a medical procedure in accordance with the usage scheme. The at least one usage-related parameter may be defined by the manufacturer of the pharmaceutical product and may be written to the memory of the container at an initial stage of the lifecycle of the pharmaceutical product and the container. The at least one usage-related parameter may also be written to the memory of the container at a later stage in the lifecycle of the pharmaceutical product, such as when the container is handed over to a patient in a pharmacy, for example.

When the use of the pharmaceutical product corresponds to an administration of the pharmaceutical product to a patient and the medical device is an administration device, the usage-related parameter may be an administration-related parameter. Performing the medical procedure may in this case comprise performing administration of the pharmaceutical product in accordance with the at least one administration-related parameter. The administration-related parameter may relate to a prescription instruction directed to ensure proper administration of the pharmaceutical product to the patient. This may include a general usage instruction for the pharmaceutical product applicable to every patient using the pharmaceutical product or a specific usage instruction prescribed by a physician to a particular patient.

For example, the at least one administration-related parameter may comprise at least one of a prescribed dosage of the pharmaceutical product, a prescribed date and/or time at which the pharmaceutical product is to be administered, a prescribed frequency and/or interval at which the pharmaceutical product is to be administered, a prescribed route of administration according to which the pharmaceutical product is to be administered, and a prescribed location and/or geographical region at which the pharmaceutical product is to be administered.

Among these parameters, the prescribed dosage of the pharmaceutical product may indicate the amount or volume (e.g., in units of ml, mg, etc.) of the pharmaceutical product to be administered, the prescribed frequency and/or interval may indicate the number of doses to be applied as well as a corresponding interval (e.g., hour, day, week, month, etc.) according to which the pharmaceutical product is to be administered, the prescribed route of administration may indicate the way through which the pharmaceutical product is to be administered to the body of the patient (e.g., oral, rectal, intra-arterial, intra-muscular, etc.), and the prescribed location may correspond to a particular treatment center at which the pharmaceutical product is to be administered, for example. The at least one administration-related parameter may be used by the administration device (or a user thereof, e.g., the patient or a clinician) to verify that the pharmaceutical product is administered at the right time, with the right dosage and/or at the right location and, therefore, assist in ensuring that the given prescription instructions are strictly adhered to.

In a variant, the administration device may be an automated administration device, i.e., an administration device which is configured to automatically administer (e.g., upon activation) the pharmaceutical product to the patient when the container is inserted in, or otherwise connected with, the administration device. An automated administration device may verify the at least one administration-related parameter before administering the pharmaceutical product to the patient. If the verification of the at least one administration-related parameter fails (e.g., the right time, the right dosage and/or the right location could not be confirmed), the administration device may refuse to perform the administration and may output a corresponding indication to the user. In one particular example, the administration device may be an (e.g., automated) injection device, wherein performing the administration may comprise injecting the patient with the pharmaceutical product. The container may in this case be an injection cartridge, for example.

Once the pharmaceutical product (or a portion thereof) has been used in a medical procedure (e.g., has been administered to the patient), usage-related information may be stored on the memory of the container in order to keep track of the usage performed. The memory of the container may thus further store usage-related information about the pharmaceutical product accommodated in the container, wherein the usage-related information may include at least one of a date of first use of the pharmaceutical product, a number of uses of the pharmaceutical product, and a remaining amount of the pharmaceutical product in the container.

The medical device may for this purpose be configured to write corresponding data to the memory of the container. If the medical device is an administration device, the usage-related information may be written to the memory of the container upon completing an administration operation. For example, if an automated administration device has completed administering a portion of the pharmaceutical product from the container to the patient, the remaining volume of the pharmaceutical product left in the container may be written to the memory of the container so that the container is kept up-to-date regarding its fill volume. When the container is used the next time with the administration device (or another administration device), the respective administration device may verify if sufficient volume is available in the container to meet the prescribed dosage specified by the administration scheme, for example.

The memory of the container may further store non-usage-related information about the pharmaceutical product accommodated in the container. Non-usage-related information about the pharmaceutical product may be information which does not specifically relate to (e.g., prescribed) usage instructions for the pharmaceutical product, but which provides information about the product itself. For example, non-usage-related information about the pharmaceutical product may include at least one of a unique identification of the pharmaceutical product, a certificate of authenticity of the pharmaceutical product, at least one storage condition for the pharmaceutical product, an expiry date of the pharmaceutical product, an identification of a manufacturer of the pharmaceutical product, an identification of a physician who prescribed the pharmaceutical product, an identification of a distributor of the pharmaceutical product, and an identification of a batch in which the pharmaceutical product was produced.

Among this information, the unique identification of the pharmaceutical product may comprise a product name or another identifier uniquely identifying the pharmaceutical product. The certificate of authenticity may be used by the medical device (or a user thereof, e.g., the patient or a clinician) to verify the genuineness of the pharmaceutical product and, as such, contribute to preventing fraud, tampering or counterfeiting with regard to the pharmaceutical product. The at least one storage condition for the pharmaceutical product may comprise indications regarding to the temperature (e.g., minimum/maximum temperature) and/or humidity (e.g., minimum/maximum humidity) at which the pharmaceutical product is to be stored. The manufacturer identification, the physician identification, the distributor (e.g., pharmacy or pharmacist) identification and the batch identification of the pharmaceutical product may be used to track the lifecycle of the container and may be used by the medical device (or a user thereof, e.g., the patient or a clinician) to verify details about the pharmaceutical product accommodated in the container. The medical device may further comprise one or more sensors (or may be configured to communicate with one or more remote sensors) in order to verify that the at least one storage condition is satisfied. To enable traceability of the container, the memory of the container may further store a unique identifier for the container.

The memory of the container may also store at least one file containing additional information about the pharmaceutical product and/or a link to a website providing additional information about the pharmaceutical product. The at least one file may comprise a document (e.g., a PDF document) or a multimedia file (e.g., a movie file), for example. The website may contain information about the pharmaceutical product which is not stored (or cannot be stored due to memory limitations) in the memory of the container itself. For example, the at least one file and/or the website may provide a more detailed product description, e.g., including illustrative images of the product, more detailed usage and prescription instructions (e.g., using illustrative movies), detailed information about the manufacturer, or the like.

In order to provide improved data security, the usage scheme may be stored in the memory of the container in an access protected manner. In one such variant, access to the usage scheme may be password protected. Thus, if a user (e.g., the patient or a clinician) wants to read the usage scheme from the memory of the container, the user may be prompted to enter a password at the medical device. Additionally or alternatively, the usage scheme may be encrypted in the memory of the container and the medical device may have a decryption key for decrypting the usage scheme. In a further variant, only selected portions of the usage scheme may be access protected. Access protection may be defined differently for read and write operations. It will be understood, that equivalent access protection may also be provided for the pairing-specific information, the usage-related information and the non-usage-related information stored in the memory of the container.

In a refinement of the system, the system may further comprise a remote server. The medical device may be configured to communicate with the remote server via wireless communication, preferably WLAN or Bluetooth communication. The remote server may reside in a cloud computing environment, for example, and may be accessible by the medical device through the Internet. Communication between the medical device and the remote server may be secured, e.g., using security protocols such as SSL, TLS, or the like.

The remote server may be used to implement various supplemental services associated with the usage of the pharmaceutical product. In one such variant, the remote server may host supplementary usage-related information accessible by the medical device. For example, the remote server may store additional usage-related parameters which are not stored (or cannot be stored due to memory limitations) in the memory of the container itself. If the medical device is an administration device, the administration device may download one or more additional administration-related parameters from the remote server and apply these parameters when performing administration of the pharmaceutical product accordingly.

Further, the medical device may be configured to exchange at least part of the data stored in the memory of the container with the remote server. In one variant, the medical device may replicate the data stored on the memory of the container (or parts thereof) on the remote server. The exchanged data may be used by the remote server to provide additional services to a user (e.g., the patient or a clinician). For example, the remote server may be configured to notify, based on an analysis of the data stored on the remote server, a user of an upcoming usage (e.g., administration) to be performed according to the usage scheme (e.g., administration scheme). Such notifications may be transmitted in the form of reminders or alarms to a user's end device, such as to the user's pager or smartphone. In another example, the remote server may be configured to report a status relating to the container and/or the medical device upon request by the user. Such report may allow the user to check the status of an ongoing usage (e.g., administration), to check the result of a completed usage (e.g., administration), to track a therapy session, or to track the entire adherence history, for example. The data stored in the remote server may also be aggregated and shared with a caregiver or healthcare provider (HCP). In another example, the data in the remote server may be stored in an electronic patient record. In an electronic patient record, further patient-related information may be stored, such as other drugs prescribed to the patient, for example. Based on the information stored in the electronic patient record, it is generally conceivable to perform an analysis and generate an alert, if one or more drugs prescribed to the patient are incompatible, for example.

In a further variant, the medical device may be instructed by the remote server to write data to the memory of the container, e.g., in order to update at least one usage-related parameter of the usage scheme or to update other data stored in the memory of the container. As an example, if it is encountered that a batch in which the pharmaceutical product was produced has been recalled due to a production fault, the remote server may instruct the medical device to write data into the memory of the container marking the container as unusable so as to prevent further use of the container. The requirement for recalling the container may be identified through the batch identification stored in the memory of the container or the remote server, respectively. If the medical device is an administration device, the administration device may be configured to verify if the container is marked as unusable and block any administration of the pharmaceutical product from the container accordingly.

In another variant, the remote server may be used as the external configuration device described above and may thus be employed to store pairing-specific information, such as a patient ID, on the medical device.

According to a second example of the present disclosure, a container accommodating a pharmaceutical product is provided. The container comprises a wireless communication unit and a memory which stores pairing-specific information for one or more medical devices. The pairing-specific information enables a medical device to verify, via wireless communication with the wireless communication unit of the container, whether the container is permitted to be used by the medical device.

According to a third example of the present disclosure, a medical device for use of a pharmaceutical product accommodated in a container is provided. The container comprises a wireless communication unit and a memory which stores pairing-specific information for one or more medical devices. The medical device is enabled for wireless communication with the wireless communication unit of the container, and the medical device is configured to read the pairing-specific information from the memory of the container to verify whether the container is permitted to be used by the medical device.

Both the container according to the second example and the medical device according to the third example may correspond to the container and the medical device described above in relation to the system according to the first example. All features described above for the container and the medical device may apply to the container according to the second example and the medical device according to the third example as well. Unnecessary repetitions are thus omitted.

In the following, the present disclosure will further be described with reference to exemplary implementations illustrated in the figures, in which.

In the following description, for purposes of explanation and not limitation, specific details are set forth in order to provide a thorough understanding of the present disclosure. It will be apparent to one skilled in the art that the present disclosure may be practiced in other implementations that depart from these specific details.

Figure 1:
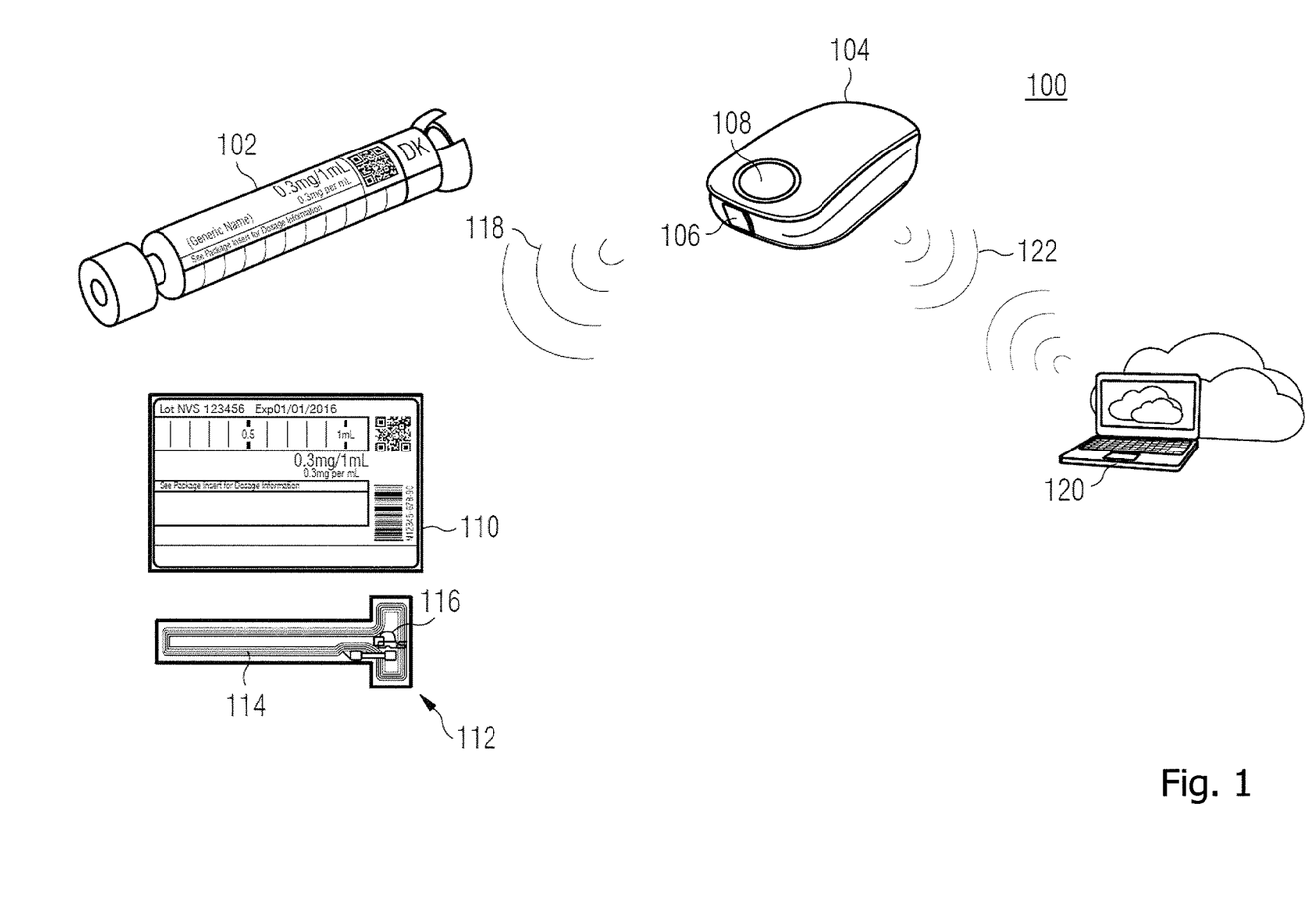
FIG. 1 illustrates an exemplary system comprising a container accommodating a pharmaceutical product, a corresponding medical device and a remote server according to the present disclosure.

FIG. 1 illustrates an exemplary system 100 for use of a pharmaceutical product according to the present disclosure. The system 100 comprises a container 102 which accommodates the pharmaceutical product as well as a medical device 104 which, in the illustrated example, is an administration device for administering the pharmaceutical product accommodated in the container 102 to a patient. More specifically, the medical device 104 is provided as an automated injection device and the container 102 is provided as an injection cartridge which accommodates the pharmaceutical product in liquid form and which has a shape-coded cylindrical form so that it may be placed into a slide-in module 106 of the medical device 104 in a form fitting manner. When the container 102 is placed into the slide-in module 106 and slid into the medical device 104 (as shown in FIG. 1), the medical device 104 may automatically dispense the pharmaceutical product from the container 102 and thereby administer the pharmaceutical product to the patient. The medical device 104 may comprise a drive mechanism for this purpose which may be configured to extend an injection needle to the outside of the device (for example at the bottom side of the medical device 104, not shown) through which the pharmaceutical product may be injected into the body of the patient. The drive mechanism may be activated by pressing a button 108 of the medical device 104 when the bottom side of the medical device 104 lies flat against the body of the patient, for example.

The container 102 comprises a printed label 110 which is affixed around the outer circumference of the container 102 and which presents information about the pharmaceutical product accommodated in the container 102 (e.g., product name, batch number, expiry date, etc.). FIG. 1 shows an exemplary label 110 for illustrative purposes additionally in an un-affixed and unwound form below the container 102. The label 110 comprises a Near Field Communication (NFC) unit 112 having an RFID antenna 114 which is integrated into the sheet of the label 110 so that it is not visible from the outside. For illustrative purposes, the NFC unit 112 is shown in FIG. 1 below the label 110 in a detached form. The NFC unit 112 comprises a memory 116 in which a usage scheme, more specifically an administration scheme, that is specifically adapted to the pharmaceutical product accommodated in the container 102 is stored. As described above, the administration scheme may specify at least one administration-related parameter to be adhered to in administering the pharmaceutical product to the patient.

The medical device 104 comprises an NFC enabled interface and is enabled for communication with the NFC unit 112 using NFC (indicated by reference numeral 118). When the container 102 is inserted into the medical device 104, the medical device 104 may read the administration scheme from the memory 116 via NFC and take into consideration the at least one administration-related parameter specified by the administration scheme for the automated administration of the pharmaceutical product to the patient. For example, when button 108 of the medical device 104 is pressed, the medical device 104 may check the prescribed date/time and/or the prescribed location specified by the administration scheme in order to verify that the pharmaceutical product is administered at the right time and/or at the right location. If the verification is successful, the medical device 104 may perform the administration of the pharmaceutical product in accordance with further administration-related parameters specified by the administration scheme, such as the prescribed dosage and/or the injection speed indicated by an administration device specific control parameter. If the verification is not successful, on the other hand, the medical device 104 may refuse to perform administration of the pharmaceutical product and output a corresponding indication to the patient.

Once the pharmaceutical product (or a portion thereof) has been administered to the patient, the medical device 104 may write usage-related information to the memory 116 of the container 102 in order to keep track of the administration performed. For example, if the container 102 was used for the first time, the medical device 104 may set the date of first use in the memory 116. Otherwise, the medical device 104 may update the number of uses of the pharmaceutical product in the memory 116. The medical device 104 may also update the remaining fill volume of the pharmaceutical product in the container 102 so that, when the container 102 is used the next time with the medical device 104 (or another administration device), the respective device may verify if sufficient fill volume is available in the container 102 to meet the prescribed dosage specified by the administration scheme before performing the next administration. Further, the usage-related information may not only be used to keep track of the administration performed but, since this information generally indicates that the container 102 has been used, it may also be used to prevent illegal container refilling by checking by the medical device 104, before an administration is performed, whether an (apparently) fully filled container has already been used or not. In a further example, usage-related information may also be stored on a memory of the medical device 104 itself in order to support partial dosing using several containers. For example, if a remaining fill volume of the pharmaceutical product in the container 102 is not sufficient to meet the prescribed dosage according to the administration scheme, the remaining fill volume may be administered, in a first administration step, from the container 102 and a value indicative of the remaining required volume to be administered to meet the prescribed dosage may be stored on the medical device 104. The container 102 may then be replaced by a fresh (e.g., fully filled) container from which the remaining required volume may then be administered by the medical device 104 in a second administration step.

As described above, in addition to the administration scheme and the usage-related information about the pharmaceutical product, the memory 116 of the container 102 may further store non-usage-related information about the pharmaceutical product and/or a file or a link to a website providing additional information about the pharmaceutical product.

As may be seen in FIG. 1, the system 100 also comprises a remote server 120 which is exemplarily illustrated by a personal/laptop computer in FIG. 1. It will be understood that any other type of computing system may be employed for the remote server 120, such as a physical or virtual server computer which may reside in a cloud computing environment, or even a smartphone, for example. Besides the NFC enabled interface, the medical device 104 also comprises a wireless communication interface and is thus enabled to communicate with the remote server 120 using wireless communication (indicated by reference numeral 122), preferably WLAN or Bluetooth. The medical device 104 may access the remote server 120 through the Internet. The communication between the medical device 104 and the remote server 120 may be secured, e.g., using security protocols such as SSL, TLS, or the like. Also, it will be understood that the medical device 104 may communicate with the remote server 120 via an intermediate device. For example, the intermediate device may be a personal computer, a laptop computer or a smartphone (e.g., of a clinician or the patient) which may communicate with the medical device 104, on the one hand, and which may communicate with the remote server 120 (e.g., a server residing in a cloud computing environment), on the other hand.

The remote server 120 may be used to implement various supplemental services associated with the administration of the pharmaceutical product. For example, the remote server may host supplementary administration-related information accessible by the medical device 104, such as additional administration-related parameters which are not stored (or cannot be stored due to memory limitations) in the memory 116 of the container 102. The administration device may download the additional administration-related parameters from the remote server 120 and apply these parameters when performing administration of the pharmaceutical product accordingly. The medical device 104 may also exchange at least part of the data stored in the memory 116 with the remote server 120. For example, the medical device 104 may replicate the data stored on the memory 116 (or parts thereof) on the remote server 120. The exchanged data may be used by the remote server 120 to provide additional services to a user (e.g., the patient or a clinician). In an example, the remote server 120 may notify, based on an analysis of the exchanged or replicated data, a user of an upcoming administration to be performed according to the administration scheme. Such notifications may be transmitted in the form of reminders or alarms to a user's pager or smartphone, for example. In another example, the remote server 120 may report a status relating to the container 102 and/or the medical device 104 upon request by the user. Such report may allow the user to check the status of an ongoing administration, to check the result of a completed administration, to track a therapy session, or to track the entire adherence history, for example. The data stored in the remote server 120 may also be aggregated and shared with a caregiver or HCP. In another example, the data in the remote server 120 may be stored in an electronic patient record. In an electronic patient record, further patient-related information may be stored, such as other drugs prescribed to the patient, for example. Based on the information stored in the electronic patient record, it is generally conceivable to perform an analysis and generate an alert, if one or more drugs prescribed to the patient are incompatible, for example.

The remote server 120 may further instruct the medical device 104 to write data to the memory 116, e.g., in order to update at least one administration-related parameter of the administration scheme or to write other data to the memory 116. As an example, if it is encountered that a batch in which the pharmaceutical product was produced has been recalled due to a production fault, the remote server 120 may instruct medical device 104 to write data into the memory 116 of the container 102 marking the container 102 as unusable so as to prevent further use of the container 102. The requirement for recalling the container 102 may be identified through the batch identification stored in the memory 116 or in the remote server 120, respectively. Before performing administration of the pharmaceutical product, the medical device 104 may verify if the container 102 is marked as unusable and block any administration of the pharmaceutical product from the container 102 accordingly.

It will be understood that the above description of the system 100 is merely exemplary and that various other implementations in accordance with the present disclosure are conceivable. For example, the pharmaceutical product does not necessarily have to be provided in liquid form and the container does not necessarily have to be a cylindrical injection cartridge. It will be understood that the principles of the present disclosure may be practiced with any other suitable form of pharmaceutical product and corresponding container, such as with tablets provided in another type of suitable packaging, for example. It will also be understood that the NFC unit of the container does not necessarily have to be provided with a label affixed to the container, but may be integrated into the container itself, for example. The skilled person will further appreciate that other types of passive wireless communication technologies (i.e., other than NFC) may be used to realize the communication between the medical device and the container. If corresponding power supply is available, the wireless communication unit of the container may even be provided as an active unit.

Moreover, it will be understood that other types of NFC enabled devices (i.e., other than the automated injection device 104) may be used to read and write data from and to the memory of the container. For example, a smartphone having required functionality (e.g., NFC functionality) to communicate with the wireless communication unit of the container may be used to read and/or write data from and to the memory. The smartphone may have a dedicated application (e.g., provided by the manufacturer of the pharmaceutical product) installed in order to provide the required functionality. For example, the smartphone may be used to read the usage scheme and/or the pairing-specific information from the container for verification by a user (e.g., the patient or a clinician) or to read other data from the memory of the container, such as non-usage-related information like the certificate of authenticity of the pharmaceutical product in order to verify the genuineness of the pharmaceutical product.

In another example, the medical device may be a non-automated administration device, such as a manually operable syringe. Similar to the automated medical device 104, a non-automated administration device may verify that the pharmaceutical product is administered at the right time and/or at the right location, for example. The non-automated administration device may output a corresponding indication for the result of the verification, e.g., via text form on a display, through an audible output, or through visual indicators, such as LEDs provided at the housing of the device.

It will further be understood that, similar to the remote server 120, the medical device 104 may be configured to communicate with other end-user devices, such as the above-mentioned external configuration device. These devices may have a dedicated application (e.g., provided by the manufacturer of the medical device) installed enabling the user to configure or view a status of the medical device 104 and, in particular, to write pairing-specific information to the medical device 104, such as a patient ID, for example. In one variant, the medical device 104 may comprise an NFC unit for this purpose so that the pairing-specific information may be written to the medical device 104 from the external configuration device via NFC.

Figure 2:
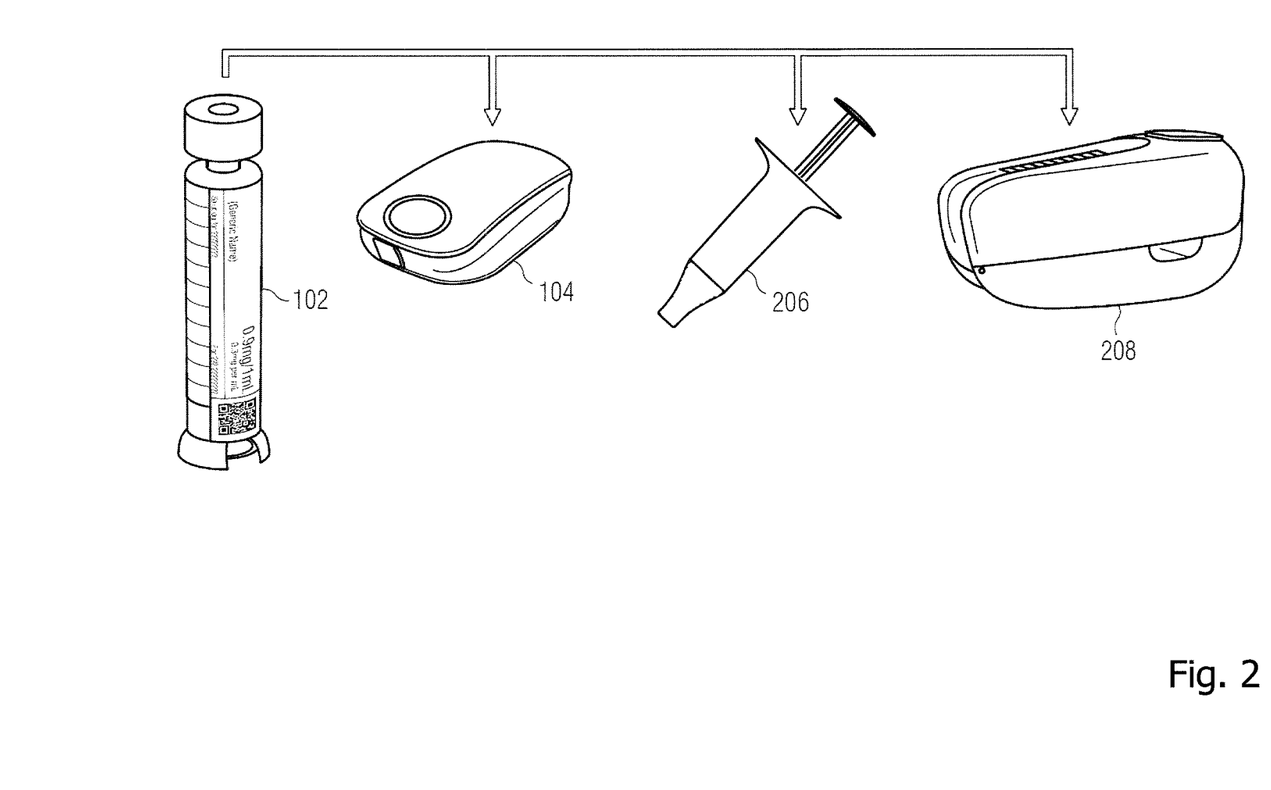
FIG. 2 illustrates that the container of FIG. 1 may interface with a plurality of types of medical devices.

FIG. 2 is an illustration which shows that the container 102 may be configured to interface with a plurality of types of medical devices. The container 102 may thus be a universal container which may be used in combination with a suite of different dedicated devices. As depicted in the example of FIG. 2, the container 102 may not only be used in combination with the automated injection device 104, but also in combination with a manually operable (i.e., non-automated) syringe 206 as well as an automated patch pump device 208. It will be understood that the medical devices 104, 206 and 208 are only exemplary and that the container 102 may also be used in combination with other types of medical devices, such as with reconstitution devices, for example, which may be used for preparing a liquid or lyophilized solution for subsequent administration. Each of the administration devices 104, 206 and 208 may have a receiving portion which may receive the container 102. The container 102 and the respective receiving portions may be shape-coded so that the container 102 may be accommodated in the receiving portions in a form fitting manner.

In order to support pairing with each of the medical devices 104, 206 and 208, the memory 116 of the container 102 may store pairing-specific information for each of these devices and, before effectively using the pharmaceutical product in a medical procedure, each of the medical devices 104, 206 and 208 may read the pairing-specific information from the memory 116 of the container 102 to verify whether the container 102 is permitted to be used by the respective medical device. More specifically, each of the medical devices 104, 206 and 208 may be configured to block use of the pharmaceutical product until the verification is complete. If a positive confirmation is determined as a result of the verification, the respective medical device may release the block so that the device may proceed with the intended medical procedure. On the other hand, if a negative confirmation is determined as a result of the verification, the respective medical device may maintain the block and thus prevent use of the pharmaceutical product in a medical procedure. In either case, an indication of the result of the verification may be provided by the respective medical device, e.g., via text form on a display, through an audible output, or through dedicated visual indicators, such as LEDs, provided at the device.

Each of the medical devices 104, 206 and 208 may store pairing-specific information itself so that the verification may be performed by comparing the pairing-specific information stored in the memory 116 of the container 102 with the pairing-specific information stored on the respective medical device, wherein a positive confirmation may only be determined in case of a match. The compared pairing-specific information may comprise, for example, a device ID of the respective medical device and/or a patient ID of the patient to which the respective medical device is assigned. In case of a comparison of device IDs, the result of the verification may indicate that the container 102 is paired with the right medical device (or the right medical device type) and, in case of a comparison of patient IDs, the result of the verification may indicate that the pharmaceutical product is applied to the right patient. Further, as the pairing-specific information stored in the memory 116 of the container 102 may also comprise at least one control parameter which may be necessary for the respective medical device to configure its own operation, the verification may also include detecting the presence of the at least one control parameter on the memory 116 of the container 102, wherein a positive confirmation may be determined in case the parameter is present and a negative confirmation may be determined in case the parameter is not present. In case of the automated injection device 104, for example, the at least one control parameter may be necessary to configure the device's injection speed of the pharmaceutical product from the container 102. It will be understood that these examples of the pairing-specific information are non-limiting and that any other type of information which enables the medical devices 104, 206 and 208 to perform the verification may be used as the pairing-specific information.

Figure 3:
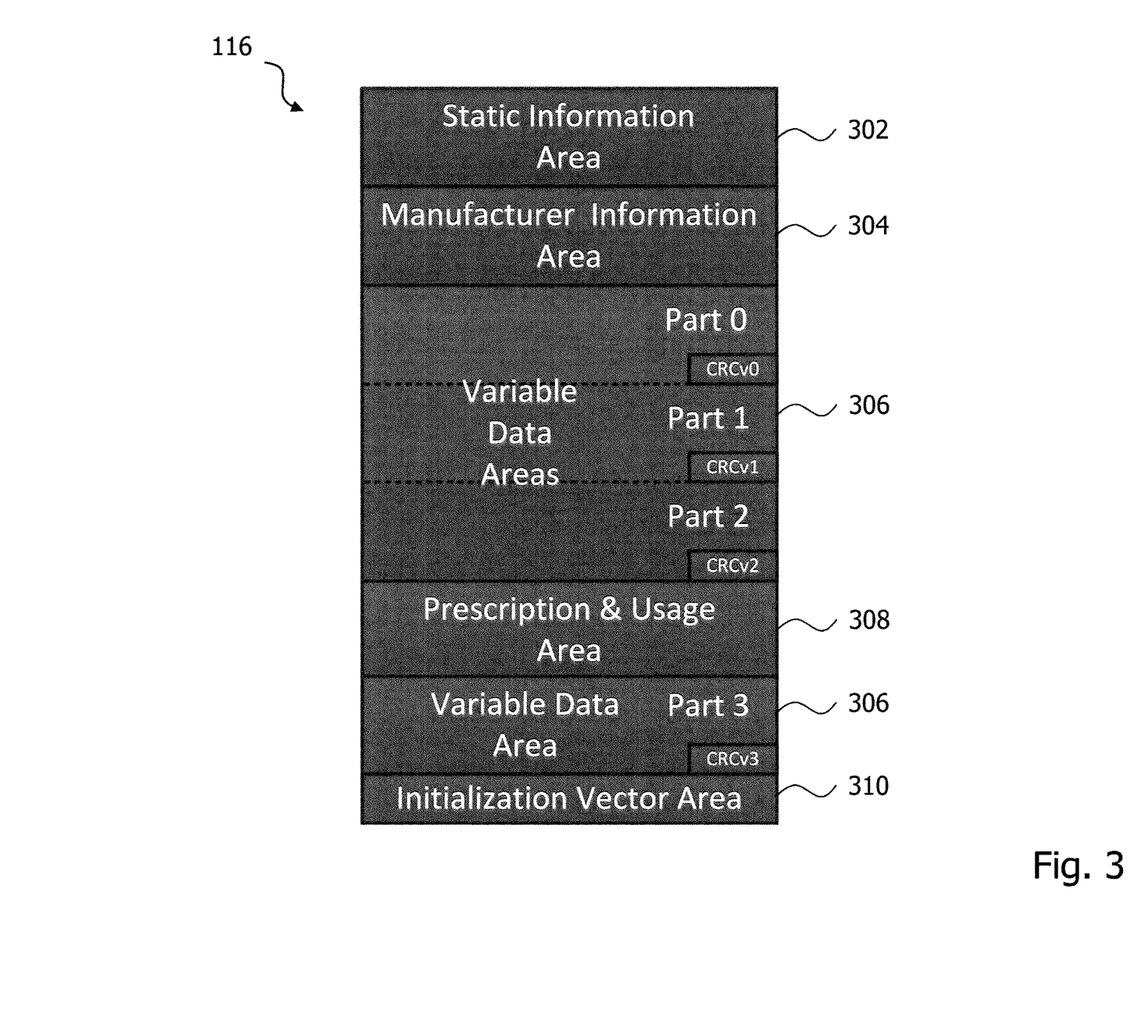
FIG. 3 schematically illustrates an exemplary memory structure of a memory of the container of FIG. 1.

FIG. 3 schematically illustrates an exemplary memory structure of the memory 116 of the container 102. As shown, the memory 116 may comprise five different types of memory areas: a static information area 302, a manufacturer information area 304, variable data areas 306, a prescription and usage area 308, and an initialization vector area 310. Among these types, the static information area 302 may be used to store unmodifiable information which may be written during manufacture and which may be write protected thereafter. This information may include the batch identification, the expiry date, the storage conditions (e.g., storage temperature/humidity) of the pharmaceutical product or a device ID of the medical device 104, for example. The manufacturer information area 304 may be used to store information which may be readable by off-the-shelf NFC enabled devices, such as NFC enabled smartphones, to allow users to identify information about the manufacturer and the pharmaceutical product without the need to use proprietary reading equipment. Information stored in the manufacturer information area 304 may include the manufacturer identification, the unique product identification or the file or link to the website providing additional information about the pharmaceutical product, for example. The information in this area may be stored in ASCII format in order to ensure its readability by off-the-shelf devices. The variable data areas 306 may be used to store miscellaneous information that may differ dependent on the pharmaceutical product accommodated in the container 102. The information stored in this area may not have a pre-defined format and a fixed location or length. Information stored in this area may include control parameters for controlling a function specific to the medical device (or the medical device type). The prescription and usage area 308 may be used to store information relevant to the prescription and usage of the pharmaceutical product. Such information may include a patient ID, the prescribed dosage, the prescribed date and/or time, the number of uses or the remaining fill volume of the container 102, for example. Finally, the initialization vector area 310 may contain information used for encryption and decryption.

Each of the memory areas may be assigned with a dedicated level of read and/or write access to implement desired access protection. For example, the static information area 302 and the manufacturer information area 304 may be freely readable, but writable by the manufacturer of the pharmaceutical product only. The variable data areas 306, the prescription and usage area 308 and the initialization vector area 310, on the other hand, may be writable by a physician or a pharmacy, but their readability may generally be restricted. Read protection may be realized by password protection, for example. Additionally or alternatively, read protection may be realized by encrypting the information stored in the respective memory areas so that only a medical device which holds the required decryption key may read from the respective memory areas.

Figure 4:
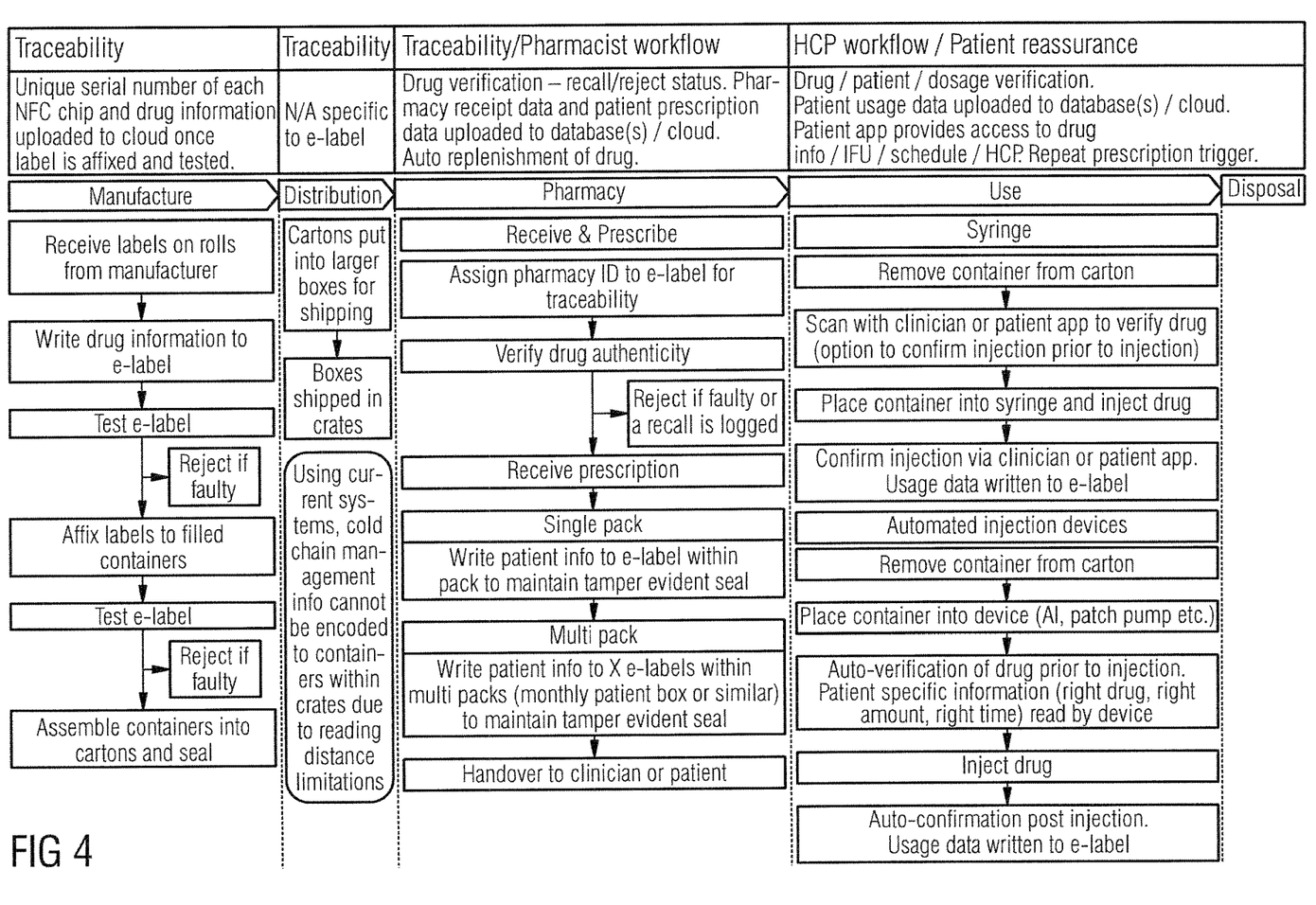
FIG. 4 illustrates an exemplary lifecycle of the container of FIG. 1 from manufacture to disposal.

FIG. 4 illustrates an exemplary lifecycle of the container 102. In FIG. 4, the terms "e-label", "drug" and "cloud" correspond to the terms "label", "pharmaceutical product" and "remote server" described above, respectively. The lifecycle may comprise the stages manufacture, distribution, pharmacy, use and disposal.

In the manufacture stage, initial information about the pharmaceutical product may be written to the memory 116 of the label 110 by the manufacturer of the pharmaceutical product (e.g., into the static and manufacturer information areas 302 and 304, as described above). The label 110 may then be affixed to the container 102 which may be prefilled with the pharmaceutical product. Tests on the NFC functionality of the label 110 may be performed before and after the affixation. Once the label 110 is successfully tested, the unique label identifier (e.g., the unique serial number of the NFC unit 112) as well as the information about the pharmaceutical product may be uploaded to the remote server 120 to ensure traceability of the container 102 and the pharmaceutical product. The container 102 may then be assembled together with other containers into a carton for distribution and sealed. In the distribution stage, the carton may be placed into a box and shipped.

In the subsequent stage, a pharmacy (or another distribution center) may receive the container 102 and write distributor identification (e.g., a pharmacy ID) to the memory 116 of the label 110 for further traceability of the container 102. Also, the pharmacy may verify the genuineness of the pharmaceutical product by checking the certificate of authenticity stored in the memory 116 of the label 110. If the verification fails, the container 102 may be marked as unusable by writing corresponding data into the memory 116 of the label 110. Further, the pharmacy may receive a patient specific prescription from a physicist and write the corresponding prescription instructions to the memory 116 of the label 110 so that the usage scheme stored in the memory 116 of the label 110 properly reflects the received prescription instructions. Also, the pharmacy may write pairing-specific information, such as a patient ID, to the memory 116 of the label 110. The data written to the memory 116 may again be uploaded to the remote server 120 and the container 102 may then be handed over to the patient or a clinician, for example.

The use stage may differ depending on which type of medical device is used for administering the pharmaceutical product from the container 102 to the patient. If a manual syringe which is not enabled for wireless communication is used, the label 110 of the container 102 may be scanned by an NFC enabled device (e.g., by a smartphone having an application provided by the manufacturer) in order to verify that the pharmaceutical product is administered to the right patient, at the right time and/or at the right location, for example. Upon completion of the injection using the syringe, the NFC enabled device may be used to write usage-related information to the memory 116 of the label 110. If, on the other hand, an automated injection device (like the automated injection device 104) is used, the container 102 may be placed into the device and the device may perform (e.g., upon activation) an automated verification of the pharmaceutical product before administering it to the patient, as described above. If the verification is successful, the device may perform automated administration of the pharmaceutical product and, upon completion, the device write usage-related information to the memory 116 of the label 110. The usage-related information may also be uploaded to the remote server 120 to keep track of the usage of the container 102. Finally, if the pharmaceutical product has been partly or fully dispensed and the container 102 is no longer usable, the container 102 may be disposed.

It is believed that the advantages of the technique presented herein will be fully understood from the foregoing description, and it will be apparent that various changes may be made in the form, constructions and arrangement of the exemplary aspects thereof without departing from the scope of the disclosure or without sacrificing all of its advantageous effects. Because the technique presented herein can be varied in many ways, it will be recognized that the disclosure should be limited only by the scope of the claims that follow.

The invention claimed is:

1. A system for use of a pharmaceutical product, comprising:
    a container accommodating a pharmaceutical product, the container being a universal container configured to interface with a plurality of medical devices of different types and comprising a wireless communication unit and a memory which stores different pairing-specific information for each of the plurality of medical devices of different types; and
    a medical device enabled for wireless communication with the wireless communication unit of the container and configured to wirelessly read the pairing-specific information from the memory of the container to verify whether the medical device is one of the plurality of medical devices for which pairing-specific information is stored in the memory of the container and whether the container is thus permitted to be used by the medical device,
    wherein the different types of the plurality of medical devices are selected from the group consisting of a syringe type, an automated injection device type, a patch pump device type and a reconstitution device type.

2. The system of claim 1, wherein the pairing-specific information comprises, for each of the plurality of medical devices, at least one of:
    an identification of the respective medical device,
    an identification of a user to which the respective medical device is assigned, and
    at least one control parameter for controlling a function specific to the respective medical device.

3. The system of claim 2, wherein the identification of the respective medical device and/or the at least one control parameter is specific to the respective medical device or specific to a device type of the respective medical device.

4. The system of claim 1, wherein the wireless communication unit of the container is a Near Field Communication, NFC, unit, and wherein the medical device is an NFC enabled device which is configured to read the pairing-specific information from the memory of the container via NFC, and/or
    wherein the container comprises a label, and wherein the wireless communication unit and the memory are included in the label.

5. The system of claim 1, wherein the medical device comprises a communication unit, and wherein pairing-specific information is writable from an external configuration device to the medical device via the communication unit, and
    wherein the communication unit is an NFC unit included in the medical device.

6. The system of claim 1, wherein the memory of the container further stores a usage scheme specifically adapted to the pharmaceutical product accommodated in the container, the usage scheme specifying at least one usage-related parameter to be adhered to in using the pharmaceutical product, and wherein the medical device is configured to read the usage scheme from the memory of the container and to perform a medical procedure in accordance with the usage scheme.

7. The system of claim 6, wherein the medical device is an administration device, and wherein performing the medical procedure comprises performing administration of the pharmaceutical product in accordance with the at least one usage-related parameter, and wherein the administration device is an injection device, and wherein performing the administration comprises injecting a patient with the pharmaceutical product.

8. The system of claim 6, wherein the at least one usage-related parameter is an administration-related parameter and comprises at least one of:

a prescribed dosage of the pharmaceutical product,
a prescribed date and/or time at which the pharmaceutical product is to be administered,
a prescribed frequency and/or interval at which the pharmaceutical product is to be administered,
a prescribed route of administration according to which the pharmaceutical product is to be administered, and
a prescribed location and/or geographical region at which the pharmaceutical product is to be administered.

9. The system of claim 1, wherein the memory of the container further stores usage-related information about the pharmaceutical product accommodated in the container the usage-related information including at least one of:

a date of first use of the pharmaceutical product,
a number of uses of the pharmaceutical product, and
a remaining amount of the pharmaceutical product in the container.

10. The system of claim 1, wherein the memory of the container further stores non-usage-related information about the pharmaceutical product accommodated in the container the non-usage-related information including at least one of:

a unique identification of the pharmaceutical product,
a certificate of authenticity of the pharmaceutical product,
at least one storage condition for the pharmaceutical product,
an expiry date of the pharmaceutical product,
an identification of a manufacturer of the pharmaceutical product,
an identification of a physician who prescribed the pharmaceutical product,
an identification of a distributor of the pharmaceutical product, and
an identification of a batch in which the pharmaceutical product was produced.

11. The system of claim 1, wherein the memory of the container further stores at least one file containing additional information about the pharmaceutical product and/or a link to a website providing additional information about the pharmaceutical product.

12. The system of claim 1, wherein the usage scheme is stored in the memory of the container in an access protected manner.

13. The system of claim 12, wherein access to the usage scheme is password protected, and/or wherein the usage scheme is encrypted in the memory of the container and the medical device has a decryption key for decrypting the usage scheme.

14. The system of claim 1, further comprising:

a remote server,
wherein the medical device is configured to communicate with the remote server via wireless communication comprising Wireless Local Area Network (WLAN) or Bluetooth communication.

15. The system of claim 14, wherein the remote server hosts supplementary usage-related information accessible by the medical device, and/or
wherein the medical device is configured to exchange at least part of the data stored in the memory of the container with the remote server, and/or
wherein the remote server is configured to notify a user of an upcoming usage to be performed according to the usage scheme, and/or
wherein the remote server is configured to report a status relating to the container and/or the medical device upon request by a user.

16. A container accommodating a pharmaceutical product, the container being a universal container configured to interface with a plurality of medical devices of different types and comprising a wireless communication unit and a memory which stores different pairing-specific information for each of the plurality of medical devices, the pairing-specific information enabling a medical device to verify, via wireless communication with the wireless communication unit of the container, whether the medical device is one of the plurality of medical devices for which pairing-specific information is stored in the memory of the container and whether the container is thus permitted to be used by the medical device, wherein the different types of the medical devices are selected from the group consisting of a syringe type, an automated injection device type, a patch pump device type and a reconstitution device type.

17. A medical device for use of a pharmaceutical product accommodated in a container, wherein the container is a universal container configured to interface with a plurality of medical devices of different types and comprises a wireless communication unit and a memory which stores different pairing-specific information for each of the plurality of medical devices, wherein the medical device is enabled for wireless communication with the wireless communication unit of the container, and wherein the medical device is configured to wirelessly read the pairing-specific information from the memory of the container to verify whether the medical device is one of the plurality of medical devices for which pairing-specific information is stored in the memory of the container and whether the container is thus permitted to be used by the medical device, and wherein the different types of the medical devices are selected from the group consisting of a syringe type, an automated injection device type, a patch pump device type and a reconstitution device type.

* * * * *

UNITED STATES PATENT AND TRADEMARK OFFICE
CERTIFICATE OF CORRECTION

PATENT NO. : 11,355,225 B2
APPLICATION NO. : 16/493733
DATED : June 7, 2022
INVENTOR(S) : Schmidlin et al.

It is certified that error appears in the above-identified patent and that said Letters Patent is hereby corrected as shown below:

On the Title Page

Item (72) (Name of Inventors), "Main Schmidlin" is changed to "Alain Schmidlin."

Signed and Sealed this
Twentieth Day of September, 2022

Katherine Kelly Vidal
*Director of the United States Patent and Trademark Office*